United States Patent
Karp et al.

[11] Patent Number: 5,851,952
[45] Date of Patent: Dec. 22, 1998

[54] HERBICIDAL THIENYLOXYAZINES

[75] Inventors: Gary Mitchell Karp; Michael Edward Condon, both of Mercer, N.J.; Axel Kleeman, Hanau, Germany; Stefan Scheiblich; Thomas Maier, both of Mainz, Germany; Halmut Siegfried Baltruschat, Schweppenhausen, Germany

[73] Assignee: American Cyanamid Company, Madison, N.J.

[21] Appl. No.: 966,486

[22] Filed: Nov. 7, 1997

[51] Int. Cl.⁶ .......................... C07D 409/12; A01N 43/40

[52] U.S. Cl. .......................... 504/251; 504/250; 504/253; 504/241; 504/242; 546/256; 546/275.4; 546/280.4; 544/333

[58] Field of Search ................ 546/256, 275.4, 546/280.4; 504/251, 250, 253

[56] References Cited

FOREIGN PATENT DOCUMENTS

| 572 093 | 5/1993 | European Pat. Off. . |
| 692 474 | 7/1995 | European Pat. Off. . |
| 693 490 | 7/1995 | European Pat. Off. . |
| 694 538 | 7/1995 | European Pat. Off. . |
| WO 94/22833 | 10/1994 | WIPO . |

*Primary Examiner*—Jane Fan
*Attorney, Agent, or Firm*—Charles F. Costello, Jr.

[57] ABSTRACT

A compound is disclosed having the formula:

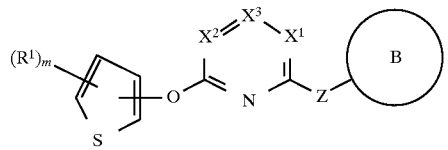

The compound is useful as an active ingredient in a herbicidal composition.

17 Claims, No Drawings

HERBICIDAL THIENYLOXYAZINES

BACKGROUND OF THE INVENTION

This invention relates to certain novel substituted 2-aryloxy-6-thienyloxy-azines, to the preparation of such compounds, to herbicidal compositions containing such compounds, and to a method of combating undesired plant growth using such compounds.

Pyridines, pyrimidines and their derivatives have many uses in the pharmaceutical area as well as in agriculture (herbicides, fungicides, acaricides, anthelmintics, bird repellents), as reagents, intermediates and chemicals for the polymer and textile industry.

Selective herbicides the active ingredients of which are pyridine derivatives, and particularly 2,6-substituted pyridines, are known from EP0572093, EP0692474 and WO 94/22833.

The European patent application EP0693490 discloses 2-phenyloxy-6-thienylmethyloxypyridines.

The European patent application EP 0694538 discloses herbicidal 2-benzyloxy-4-phenoxypyrimidines.

However, disubstituted pyridine and pyrimidine derivatives containing a thienyloxy group have not yet been described.

Although many of the known compounds show considerable activity against various weeds, they are not completely satisfying with regard to their selectivity or because of their persistence.

The compounds according to the present invention combine high herbicidal activity with the necessary selectivity and enhanced soil degradation.

SUMMARY OF THE INVENTION

We have now found that, surprisingly, 2-aryloxy-6-thienyloxy-pyridines, 6-aryloxy-2-thienyloxy-pyrimidines, 2-aryloxy-6-thienyloxy-pyrimidines and 6-aryloxy-2-thienyloxy-pyrazines show excellent herbicidal activity at low dosages combined with higher selectivity in crops than those disclosed in the aforementioned patent applications.

Accordingly, the present invention provides novel compounds of the general formula I

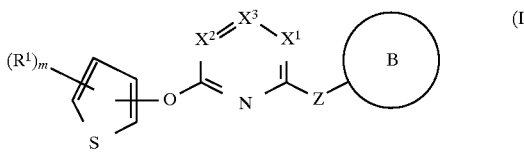

wherein
one of the groups $X^1$, $X^2$ and $X^3$ represents N or CY and the others represent CY, in which Y each independently represent a hydrogen atom or have the meaning given for $R^2$;
$R^1$ and $R^2$ each independently represent a halogen atom or an optionally substituted alkyl, alkenyl, alkinyl, alkoxy, alkoxyalkyl, alkoxyalkoxy, group or a haloalkyl, haloalkoxy, cyano, nitro or $SF_5$ group; or $-S(O)_p-R^3$, in which p is 0, 1 or 2, and $R^3$ represents an alkyl or haloalkyl group; or
$-NR^4R^5$, in which $R^4$ and $R^5$ each independently represent a hydrogen atom, an alkyl, alkenyl, aralkyl or aryl group, or $R^6O-CY'-$, in which $R^6$ represents an alkyl group, and Y' represents O or S;
B represents an optionally substituted aryl group, an optionally substituted 5- or 6- membered nitrogen-containing heteroaromatic group or an optionally substituted thienyl group;

Z represents an oxygen or sulfur atom or a $-OCH_2-$ or $-SCH_2-$ group;
m is 0 or an integer from 1 to 3.

The compounds show excellent selective herbicidal activity in certain crops, such as maize and rice, and enhanced soil degradation.

It is another object of the invention to provide methods for controlling undesired plant growth by contacting said plants with a herbicidally effective amount of the new compounds.

It is another object of the invention to provide selective herbicidal compositions containing the new compounds as active ingredients.

It is another object of the invention to provide new processes for the preparation of the new compounds.

Those and other objects and features of the invention will become more apparent from the detailed description set forth hereinbelow.

DETAILED DESCRIPTION OF THE PREFERRED EMBODIMENTS

It has surprisingly been found that the novel compounds of formula I in which B, $R^1$, $R^2$, $R^3$, $R^4$, $R^5$, $R^6$, $X^1$, $X^2$, $X^3$, Y, Z and m have the meaning given above for formula I show an excellent herbicidal activity against a broad range of weeds.

Generally, if any of the above mentioned moieties comprises an alkyl, alkenyl or alkynyl group, such groups, unless otherwise specified, may be linear or branched and may contain 1 to 6, preferably 1 to 4, carbon atoms. Examples of such groups are methyl, ethyl, propyl, vinyl, allyl, propargyl, isopropyl, butyl, isobutyl and tertiary-butyl groups. The alkyl portion of a haloalkyl, haloalkoxy, haloalkylthio, alkylthio or alkoxy group suitably has from 1 to 4 carbon atoms, preferably 1 or 2 carbon atoms. The number of carbon atoms in the alkoxyalkyl, alkoxyalkoxy or dialkoxyalkyl groups is up to 6, preferably up to 4, e.g. methoxymethyl, methoxymethoxy, methoxyethyl, ethoxymethyl, ethoxyethoxy, dimethoxymethyl.

"Halogen" means a fluorine, chlorine, bromine or iodine atom, preferably fluorine, chlorine or bromine. Haloalkyl moieties of any groups within the definitions used herein and as such can contain one or more halogen atoms. Haloalkyl, haloalkoxy and haloalkylthio are preferably mono-, di-, tri- or perfluoroalkyl, -alkoxy and -alkylthio, especially trifluoromethyl, chlorodifluoromethyl, pentafluoroethyl, trifluoromethoxy, difluoromethoxy, difluoromethylthio, trifluoromethylthio, 2,2,2-trifluoroethyl, 1,1,1-trifluoroprop-2-yl or 2,2,2-trifluoroethoxy groups.

An aryl group as substituent or part of other substituents is suitably an optionally substituted phenyl group. An heteroaryl group as substituent or part of other substituents is suitably an optionally substituted 5- or 6-membered heterocycles containing one or more heteroatoms selected from nitrogen, oxygen and sulfur, 1 sulfur atom or 1 to 3 nitrogen atoms being preferred. Examples of such groups are thienyl, pyrazolyl, imidazolyl, triazolyl, tetrazolyl, thiazolyl, pyridyl, pyrazinyl, pyrimidyl, pyridazinyl, and triazinyl groups. 5- or 6-membered heterocycles may be fused with a benzene ring.

"Aryl" and "heteroaryl" preferably represent a phenyl, pyridyl, thienyl or pyrazolyl group being substituted by one or more of the same or different substituents selected from halogen atoms, alkyl groups, alkoxy groups, cyano groups, haloalkyl groups, haloalkoxy groups, alkylthio groups, haloalkylthio groups and $SF_5$ groups.

When any groups are designated as being optionally substituted, the substituent groups which are optionally present may be any of those customarily employed in the modification and/or development of pesticidal compounds and are especially substituents that maintain or enhance the herbicidal activity associated with the compounds of the present invention, or influence persistence of action, soil or plant penetration, or any other desirable property of such herbicidal compounds.

There may be one or more of the same or different substituents present in each part of the molecules. In relation to moieties defined above as comprising an optionally substituted alkyl group, including alkyl parts of haloalkyl, alkoxy, alkylthio, haloalkoxy, alkylamino and dialkylamino groups, specific examples of such substituents include phenyl, halogen atoms, nitro, cyano, hydroxyl, $C_{1-4}$-alkoxy, $C_{1-4}$-haloalkoxy and $C_{1-4}$-alkoxycarbonyl groups.

In relation to moieties defined above as comprising an optionally substituted aryl or heteroaryl group, optional substituents include halogen, especially fluorine, chlorine and bromine atoms, and nitro, cyano, amino, hydroxy, phenoxy, $C_{1-4}$-alkyl, $C_{1-4}$-alkoxy, $C_{1-4}$-haloalkyl, $C_{1-4}$-haloalkenyl, $C_{1-4}$-haloalkoxy, $C_{1-4}$-haloalkylthio, $C_{1-4}$-alkylsulfonyl and halosulfanyl groups such as $SF_5$. In the case of phenyl-groups 1 to 5 substituents may suitably be employed, in the case of thienyl-groups 1 to 3 substituents may suitably be employed, 1 or 2 substituents being preferred.

Typically haloalkyl, haloalkoxy and haloalkylthio groups are trifluoromethyl, pentafluoroethyl, 2,2,2-trifluoroethyl, 1,1,1-trifluoroprop-2-yl, trifluoromethoxy, difluoromethoxy, 2,2,2-trifluoroethoxy and trifluoromethylthio groups.

Preferably m is 0, or m is 1 or 2, in particular 1. When m is at least 1, one substituent $R^1$ is most preferably located at the 5-position.

At least two of the groups $X^1$ through $X^3$ represents CY. Preferably $X^2$ and $X^3$ or $X^1$, $X^2$ and $X^3$ denote CY.

$X^1$ preferably is N or CY, in particular N, CH or CF;

$X^2$ preferably is CY, in particular CH or CF; and $X^3$ preferably is CY in particular $CR^2$.

The thienyloxy group may be attached in the 2- or 3-position with respect to the sulfur atom. 3-thienyloxy groups are preferred.

In formula I the ring B preferably represents a group of formula a, b, c or d:

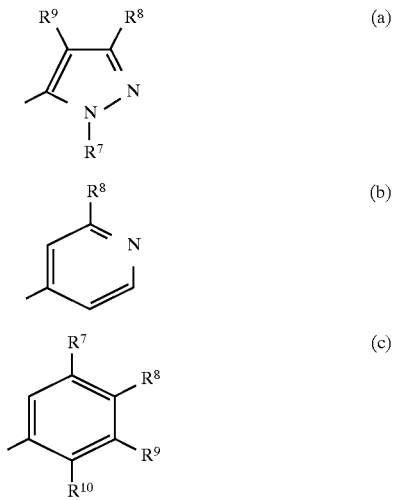

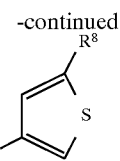

wherein
$R^7$, $R^8$, $R^9$ and $R^{10}$ each independently represent a hydrogen atom or halogen atom or an optionally substituted alkyl or alkoxy group.

particularly preferred are the compounds of formula IA and IB

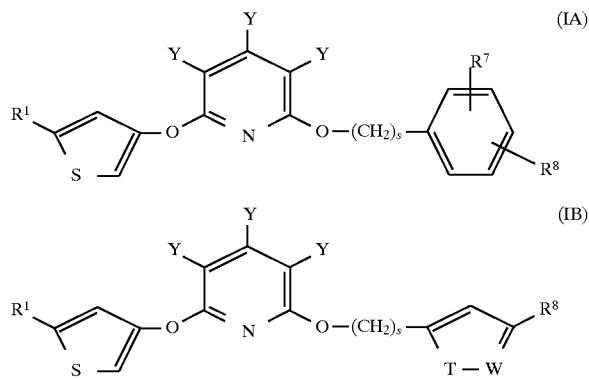

wherein $R^1$ has the meaning given above; $R^7$ represents a hydrogen or halogen atom or a haloalkyl group; and $R^8$ represents an hydrogen or halogen atom or a haloalkyl group, the groups Y in the 3- and 5-position represent a hydrogen or fluorine atom and the group Y in the 4-position has the meaning given for $R^2$, W represents a N or S atom, T represents a —CH—, —CH=CH— or a —N(CH$_3$)— group, and T and s is 0 or 1.

At least one of $R^7$ and $R^8$ preferably represents a hydrogen, if s is 1, or $R^8$ is attached in the 4-position and represents a hydrogen atom, and $R^7$ is attached in the 2- or 3-position and represents a halogen atom or a haloalkyl group, if is s is 0.

Suitably, $R^1$ represents a halogen atom or an optionally substituted alkyl, alkoxy, alkyl thio or cyano group.

Preferably, $R^1$ represents an optionally substituted $C_{1-6}$ alkyl, $C_{1-6}$ alkoxy or $C_{1-6}$ alkylthio group which is unsubstituted, or substituted by one or more moieties independently selected from halogen atoms. In particular $R^1$ denotes a fluorine or chlorine atom or a methyl, ethyl, iso-propyl or tert-butyl, methoxy, trifluoromethyl, perfluoroethyl, trifluormethoxy,difluoromethoxy, trifluormethylthio or difluoromethylthio group.

Preferably, $R^2$ represents a cyano group or a $C_{1-6}$ alkyl, $C_{1-6}$ alkoxy or $C_{1-6}$ alkylthio group which is unsubstituted, or substituted by one or more moieties independently selected from halogen atoms. In particular $R^2$ denotes a fluorine or chlorine atom or a methyl, ethyl, methoxy, methylthio or a cyano group.

The invention is exemplified by the following specific compounds:

2,6-bis-(5-trifluoromethylthien-3-yloxy)-4-methylpyridine 2-(4-fluorobenzyloxy)-6-(5-trifluoromethylthien-3-yloxy)-4-methylpyridine 2-(3,4-difluorobenzyloxy)-6-(5-trifluoromethylthien-3-yloxy)-4-methylpyridine 2-(2,4-difluorobenzyloxy)-6-(5-trifluoromethylthien-3-yloxy)-4-methylpyridine, 2-(3-trifluoromethylphenoxy)-6-(5-trifluoromethylthien-3-yloxy)-4-methylpyridine, 2-(3,4-dichlorophenoxy)-6-(5-trifluoromethylthien-3-yloxy)-4-cyanopyridine,
2-(3,4-dichlorophenoxy)-6-(5-trifluoromethylthien-3-yloxy)-4-methylpyridine,
3,5-difluoro-2-(4-fluorobenzyloxy)-6-(5-trifluoromethylthien-3-yloxy)-4-methylpyridine,
3,5-difluoro-2-(3,4-difluorophenoxy)-6-(5-trifluoromethylthien-3-yloxy)-4-methylpyridine,
3,5-difluoro-2-(3-chloro-4-fluorophenoxy)-6-(5-trifluoromethylthien-3-yloxy)-4-methylpyridine,
2-benzyloxy-6-(5-trifluoromethylthien-3-yloxy)-4-cyanopyridine,
2-benzyloxy-6-(5-trifluoromethylthien-3-yloxy)-4-methylpyridine,
2-(3-chloro-4-fluorophenoxy)-6-(5-trifluoromethylthien-3-yloxy)-4-methylpyridine,
2-(thien-2-ylmethyloxy)-6-(5-trifluoromethylthien-3-yloxy)-4-methylpyridine,
2-(2,4-difluorobenzyloxy)-6-(5-trifluoromethylthien-3-yloxy)-4-methoxypyridine,
2-(4-fluorobenzyloxy)-6-(5-trifluoromethylthien-3-yloxy)-4-methoxypyridine,
2-(3-trifluoromethylphenyloxy)-6-(5-trifluoromethylthien-3-yloxy)-4-methoxypyridine,
3,5-difluoro-2-(3-fluorophenoxy)-6-(5-trifluoromethylthien-3-yloxy)-4-methoxypyridine,
3,5-difluoro-2-benzyloxy-6-(5-trifluoromethylthien-3-yloxy)-4-methoxypyridine,
3,5-difluoro-2-(3-chlorophenoxy)-6-(5-trifluoromethylthien-3-yloxy)-4-methoxypyridine,
2-benzyloxy-6-(5-trifluoromethylthien-3-yloxy)-4-methoxypyridine,
2-(3,4-dichlorophenoxy)-6-(5-trifluoromethylthien-3-yloxy)-4-methoxypyridine,
2-(3-chloro-4-fluorophenoxy)-6-(5-trifluoromethylthien-3-yloxy)-4-methoxypyridine,
2-(2,4-difluorobenzyloxy)-6-(5-trifluoromethylthien-3-yloxy)-pyridine,
2-(4-fluorobenzyloxy)-6-(5-trifluoromethylthien-3-yloxy)-pyridine,
2-(3-trifluoromethylphenyloxy)-6-(5-trifluoromethylthien-3-yloxy)-pyridine,
3,4,5-trifluoro-2-(3,4-difluorophenoxy)-6-(5-trifluoromethylthien-3-yloxy)-pyridine,
3,4,5-trifluoro-2-(3,4-difluorobenzyloxy)-6-(5-trifluoromethylthien-3-yloxy)-pyridine,
2,4-bis(5-trifluoromethylthienyl-3-oxy)-6-methoxypyrimidine,
2-benzyloxy-4-(5-trifluoromethylthienyl-3-oxy)-6-methoxypyrimidine,
2-benzylthio-6-(5-trifluoromethylthienyl-3-oxy)-4-methylpyridine,
2-(3trifluormethylphenylthio)-6-(5-trifluoromethylthienyl-3-oxy)-4-methylpyridine,
2-(3-chloropyrid-4-yloxy)-6-(5-trifluoromethylthienyl-3-oxy)-4-methylpyridine,
2-(3-trifluoromethylpyrid-4-yloxy)-6-(5-trifluoromethylthienyl-3-oxy)-4-methylpyridine,
2-(3-difluoromethoxypyrid-4-yloxy)-6-(5-trifluoromethylthienyl-3-oxy)-4-methylpyridine, and
2-(1-methyl-3-trifluoromethylpyrazol-5-yloxy)-6-(5-trifluoromethylthienyl-3-oxy)-4-methylpyridine.

The compounds are oils, gums, or, predominantly, crystalline solid materials. They are superior through their valuable herbicidal properties. For example, they can be used in agriculture or related fields for the control of undesired plants. The compounds of general formula I according to the invention possess a high herbicidal activity within a wide concentration range and at low dosages, and may be used in agriculture without any difficulties, in particular for the selective control of undesired plants such as *Alopecurus myosuroides*, *Echinochloa crus-galli*, *Setaria viridis*, *Galium aparine*, *Stellaria media*, *Veronica persica*, *Lamium purpureum*, *Viola arvensis*, *Abutilon theophrasti*, *Ipomoea purpurea* and *Amaranthus retroflexus* by pre- and post-emergence application, particularly in certain crops, such as maize and rice.

The compounds according to the invention can be prepared by conventional methods, particularly as follows:

(A) A suitable process for the preparation of the compounds of general formula I comprises the reaction of a compound of formula II:

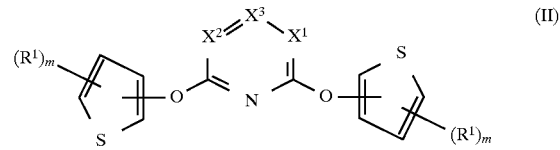

in which $R^1$, $R^2$, $X^1$, $X^2$, $X^3$ and m have the meaning given, with a compound of general formula III,

in which B and Z have the meaning given, or a metal salt thereof.

(B) The compounds of formula II may be prepared from the compounds of the general formula IV,

in which $R^2$, $X^1$, $X^2$ and $X^3$ have the meaning given and L is a leaving group with a compound of formula V,

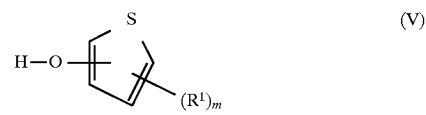

or a metal salt thereof.

(C) A suitable process for the preparation of the compounds of general formula I comprises the reaction of a compound of formula VI:

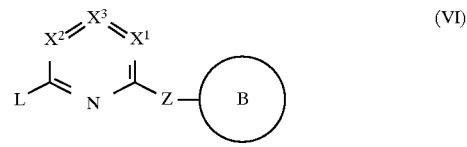

in which B, $R^1$, $R^2$, $X^1$, $X^2$, $X^3$ and Z have the meaning given and L is a leaving group, with a compound of general formula V or a metal salt thereof.

The reactions according to (A), (B) and (C) may be carried out in the absence or presence of a solvent which promotes the reaction or at least does not interfere with it. Preferred are polar, aprotic or protic solvents, suitably being N,N-dimethylformamide, dimethylsulfoxide, sulfolane, acetonitrile, methyl ethyl ketone, or an ether, such as tetrahydrofurane or dioxane, or alcoholes, or water, or mixtures thereof. The reaction is carried out at a temperature between ambient temperature and the reflux temperature of the reaction mixture, preferably at elevated temperature, especially at reflux temperature. Conveniently substantially equimolar amounts of reactants are used. It may be expedient, however, to use one reactant in excess.

The reactions may be carried out in the presence of a basic compound such as an alkali hydroxide, bicarbonate or carbonate, e.g. sodium or potassium hydroxide, bicarbonate or carbonate, an alkali alkoxide, e.g. sodium ethoxide, or an organic base such as triethylamine.

A hydroxy compound used in the above reactions may be present in form of a salt, preferably as a salt of an alkali metal, particularly of sodium or potassium. The presence of a copper salt may be suitable.

Suitable leaving groups L are e.g. alkyl- and arylsulfonyl, alkyl- and arylsulfonyloxy, perfluoroalkylsulfonyloxy, nitro and halogen, particularly fluorine, chlorine and bromine groups.

The metal salts are conveniently generated by reaction of the hydroxythiophene of formula V or B —Z— H compounds of formula III, the alcohols or thiols with a suitable metal base, a metal carbonate or hydride.

The prepared compounds of formula I may be isolated and purified using conventional methods and techniques.

The starting compounds for the preparation of compounds of this invention can be prepared according to known methods.

For compounds of formula II or IV, certain substituents $R^2$ like alkyl, alkoxy, alkylthio, alkylamino, dialkylamino, amino or halo, can be introduced onto the pyridine ring by displacement of a alkyl- or arylsulfonyl, alkyl- or arylsulfonyloxy, nitro, or halogen group. Halogen atoms may also be introduced by diazotization of an amino group. The diazotization reaction may be carried out in an aqueous medium and the diazonium compound can be reacted e.g. with CuCl, CuBr, CuCN or KI to introduce the chlorine, bromine, iodine atom or the cyano group.

The compounds used as starting material are partly known and partly novel. The intermediate compounds of formula IV are known for example from GB 2 285 045. Intermediates of formula VI are known from WO 94/22833, EP 572093, EP 693490, EP 692474, EP 694538, EP 707001 and GB2285045.

The invention relates to the novel intermediates, in particular to the compounds of formula II and formula VA,

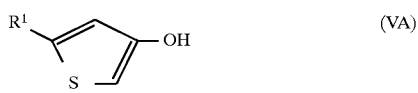

in which $R^1$ has the meaning given, which can be prepared analogously to known methods.

Intermediates of formula VA can suitably be prepared according to the following reaction scheme:

Scheme I:

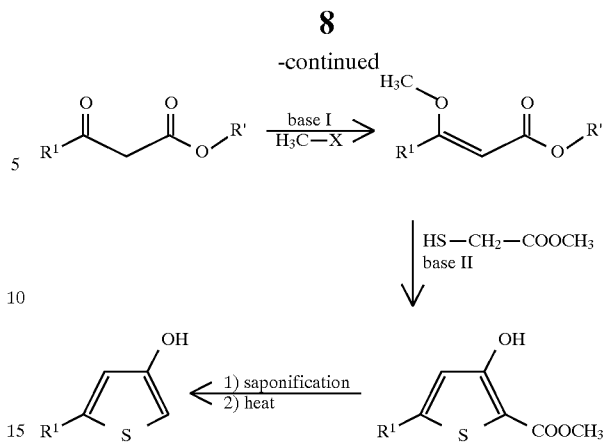

in which $R^1$ has the meaning given above, and R' represents an $C_{1-6}$ alkyl group, X is a halogen atom or a tosylate group, base I represents a strong base, e.g. $Cs_2CO_3$ and base II represents a alkali hydroxide, e.g. sodium hydroxide. The saponification and decarboxylation reaction is carried out under conventional conditions.

Alternatively, the compound of formula VA may suitably be prepared according to the following reaction scheme:

Scheme II:

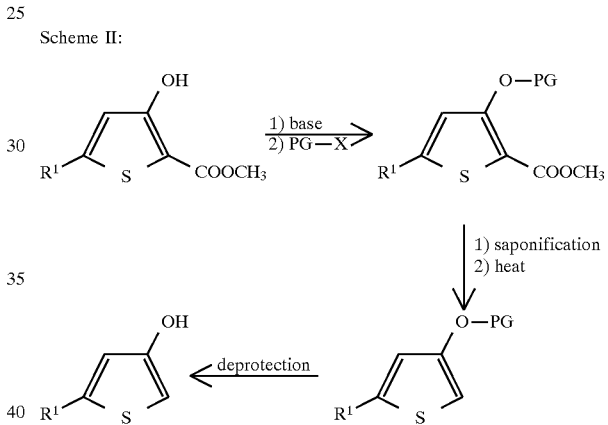

in which $R^1$ has the meaning given above and represents preferably haloalkyl, in particular perfluoroalkyl such as trifluoromethyl, and PG represents a protecting group, in particular a benzyl group, and X represents a suitable leaving group, preferably a halogen atom, in particular a chloro or bromo atom. The deprotection method depends on the protecting group used. When the protectiong group represents a benzyl group, treatment with iodotrimethylsilane in tetrachloromethane is preferred.

The present invention also provides the use of the compounds of formula I as herbicides. Further, in accordance with the invention there is provided a method of combating undesired plant growth at a locus by treating the locus with a composition according to the invention or an effective amount of a compound of formula I. As a useful action is by foliar spray application, the locus is most suitably the plants in a crop area, typical crops being cereals, maize, soya bean, sunflower or cotton. However, application may also be to the soil for those compounds having pre-emergence herbicidal action, or to the water of paddy rice fields. The dosage of active ingredient used may, for example be in the range of from 0.005 to 3 kg/ha, preferably 0.01 to 1 kg/ha.

The compounds of general formula I have been found to show interesting activity as herbicides. Accordingly, the invention further provides a herbicidal composition comprising a compound of formula I as defined above in association with at least one carrier, and a method of making such a composition which comprises bringing a compound of formula I into association with at least one carrier. Preferably, there are at least two carriers, at least one of which is a surface-active agent.

The invention also provides a method of combating undesired plant growth at a locus, comprising application of such a compound or composition.

Particularly interesting activity has been found against grasses and broad leaf weeds, pre- and post-emergence. Selectivity in important crop species such as wheat, barley, maize, rice and soya-beans has also been found. This activity provides a further aspect of the present invention.

In a method as mentioned above, the dosage of the active ingredient, the compound of general formula I, may, for example, be from 0.005 to 10 kg/ha, suitably 0.01 to 4 kg/ha. The locus may be an agricultural or horticultural locus, comprising, for example, a plant or soil. In a preferred method the locus contains undesired plant growth and treatment is by foliar spray application.

The invention also provides the use of a compound as defined above, as a herbicide. A carrier in a composition according to the invention is any material with which the active ingredient is formulated to facilitate application to the locus to be treated, or to facilitate storage, transport or handling. A carrier may be a solid or a liquid, including a material which is normally gaseous but which has been compressed to form a liquid, and any of the carriers normally used in formulating pesticidal compositions may be used. Preferably, compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosene and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus, preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be non-ionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkaryl sulphonates such as dodecylbenzene sulphonate; and polymers of ethylene oxide and copolymers of ethylene oxide and propylene oxide.

The compositions of the new invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing 0.5–10% w of active ingredient. Granules are usually prepared to have a particle size between 10 and 100 BS mesh (1.676–0.152 mm), and may be manufactured by agglomeration or impregnation techniques. Generally, granules will contain 0.5–75% w active ingredient and 0–10% w of additives such as stabilisers, surfactants, slow release modifiers and binding agents. The so-called 'dry flowable powders' consist of relatively small granules having a relatively higher concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The active ingredients according to the invention can be employed alone or as formulations in combination with conventional herbicides. Such combinations of at least two herbicides can be included in the formulation or also added in a suitable form with the preparation of the tank mix. For such mixtures at least one of the following known herbicides can be used:

amethydione, metabenzthiazuron, metamitron, metribuzin, 2,4-D, 2,4-DB, 2,4-DP, alachlor, alloxydim, asulam, atrazin, bensulfuron, bentazon, bifenox, bromoxynil, butachlor, chloridazon, chlorimuron, chlorpropham, chlorsulfuron, chlortoluron, cinmethylin, clopyralid, cyanazin, cycloate, cycloxydim, dichlobenil, diclofop, eptame, ethiozin, fenoxaprop, fluazifop, fluometuron, fluridone, fluroxypyr, fomesafen, glyphosate, haloxyfop, hexazinone, imazamethabenz, imazapyr, imazaquin, imazethapyr, ioxynil, isoproturon, lactofen, MCPA, MCPP, mefenacet, metazachlor, metolachlor, metsulfuron, molinate, norflurazon, oryzalin, oxyfluorfen, pendimethalin, picloram, pretilachlor, propachlor, pyridate, quizalofopethyl, sethoxydim, simetryne, terbutryne, thiobencarb, triallate, trifluralin, diflufenican, propanil, triclopyr, dicamba, desmedipham, acetochlor, fluoroglycofen, halosafen, tralkoxydim, amidosulfuron, cinosulfuron, nicosulfuron, pyrazosulfuron, oxasulfuron, azimsulfuron, thiameturon, thifensulfuron, triasulfuron, tribenuron, esprocarb, prosulfocarb, terbutylazin, benfuresate, clomazone, di-methazone, dithiopyr, isoxaben, quinchlorac, qinmerac, sulfosate, cyclosulfamuron, imazamox, imazamethapyr, flamprop-M-methyl, flamprop-M-isopropyl, picolinafen, thiafluamide, isoxaflutole, flurtamone, daimuron, bromobutide, methyldimron, dimethenamid, sulcotrione, sulfentrazone, oxadiargyl, acifluorfen, cafenstrole, carfentrazone, diuron, glufosinate.

Mixtures with other active ingredients like fungicides, insecticides, acaricides and nematicides are possible.

A formulation containing a compound according to the invention can consist of 100 g of active ingredient (compound of formula I), 30 g of disperging agent, 3 g of antifoaming agent, 2 g of structure agent, 50 g of anti-freezing agent, 0.5 g of a biocidal agent and water ad 1000 ml. Prior to use it is diluted with water to give the desired concentration of active ingredient.

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

The structures of the compounds prepared in the following examples were additionally confirmed by NMR and mass spectrometry.

EXAMPLE 1

Preparation of 3-hydroxy-5-trifluoromethylthiophene
Method A
1A Ethyl 3-methoxy-3-trifluoromethylacrylate Cesium carbonate (132.8 g) was added to a mixture of ethyl 4,4,4-trifluoroacetoacetate (75.0 g) and dimethylformamide (400 ml). The reaction mixture was heated to 70° C. for 30 minutes. A mixture of methyl tosylate (83.4 g) and dimethylformamide (150 ml) was added to the resulting reaction mixture within 40 minutes. The mixture was heated for 3 hours and cooled to room temperature. Upon dilution with water (800 ml) the reaction mixture was extracted with diethyl ether three times. The combined organic phases were washed with water and dried. The mixture was concentrated and the residue distilled under reduced pressure to 30 yield the product as a clear liquid (48.5 g, 60%) with a boiling point of 62°–70° C. at 12 mm.

1B Methyl (3-hydroxy-5-trifluoromethylthien-2-yl)-carboxylate

A solution of 1M potassium hydroxide in methanol (30 ml) is added to a cooled mixture of 1A (4.6 g), methyl thioglycolate (2.46 g) and methanol (10 ml). The resulting reaction mixture was stirred for 24 hours at room temperature. Then the mixture was poured on ice and acidified with 6N sulfuric acid (pH=2). The mixture is extracted with diethyl ether twice. The combined organic phases were washed with water and dried. The mixture was concentrated and the residue is distilled under reduced pressure to yield the product as a clear liquid (3.4 g, 65%) with a boiling point of 42°–45° C. at 0.10 mm.

1C (3-Hydroxy-5-trifluoromethylthien-2-yl)-carboxylic acid

A mixture of 1B (2.38 g) and methanol (20 ml) was added to a stirred solution of sodium hydroxide (1.68 g) in water (20 ml). The reaction mixture was heated at reflux for 3 hours. The reaction mixture was cooled to room temperature and concentrated in vacuo. The concentrate was cooled to 5° C. and acidified with concentrated HCl (3.5 ml). The resulting suspension was stirred at 5° C. for 30 minutes. The solid was collected by filtration, washed with water, then dried in vacuo at 35°–40° C. to give the free acid (1.45 g, 65%).

1D 3-Hydroxy-5-trifluoromethylthiophen 1C (1.80 g) was slowly heated under argon. Evolution of gas was observed at 90° C. Heating was continued for additional 3.5 hours at 90° C. The resulting oil was distilled under reduced pressure (boiling point 70°–74° C. at 4 mm) to yield 1.18 g (82%) of compound 1D.

Method B
1E Methyl (3-benzyloxy-5-trifluoromethylthien-2-yl)-carboxylate

A mixture of 1B (5.0 g) and dimethylformamide (50 ml) is treated with sodium hydride (1.06 g). Benzylbromide (3.15 ml) was slowly added to the resulting reaction mixture and stirred at room temperature for 20 hours. The reaction mixture was poured into water. The mixture was extracted with diethyl ether twice. The combined organic phases were washed with water, dried and concentrated in vacuo. The crude product was chromatographed (hexane/dichloromethane, 1/1) to give the product as a white solid (4.5 g, 64%) with a melting point of 52°–53.5° C.

1F (3-Benzyloxy-5-trifluoromethylthien-2-yl)-carboxylic acid

A mixture of 1E (3.80 g) and tetrahydrofuran (12 ml) was heated to reflux in 2N sodium hydroxide (12 ml) for 12 hours. Then the mixture was poured on ice and acidified with 6N sulfuric acid (pH=1–2). The mixture is extracted with diethyl ether twice. The combined organic phases were washed with water and dried. The mixture was concentrated and the residue is distilled under reduced pressure to yield the product as a white solid (3.22 g, 89%) with a melting point of 142°–144° C.

1G 3-Benzyloxy-5-trifluoromethylthiophen

A mixture of 1F (14.5 g) and quinoline (50 ml) was treated with copper powder (4.57 g) and heated to 150° C. The reaction mixture is heated for 25 minutes at 150° C. and cooled to room temperature. The mixture was filtered and washed with water. Aqueous quinoline was acidified with 6N HCl (pH=2) and extracted with diethyl ether twice. The combined organic phases were washed with water and dried. The mixture was concentrated and the residue was chromatographed to yield a yellow liquid ( 8.74 g, 71%).

1D 3-Hydroxy-5-trifluoromethylthiophen

A mixture of 1G (7.75 g) and tetrachloromethane (50 ml) was treated with iodotrimethylsilane (12.30 ml) and heated to 60° C. for 12 hours. The reaction mixture was stirred at room temperature for 12 hours. Water (50 ml) was added and the resulting reaction mixture was extracted with dichloromethane three times. The combined organic phases were washed with water and dried. The crude reaction mixture was eluted through hexane (100 g/silica gel) to remove benzyliodide and then with diethyl ether. The etheral phases were concentrated and distilled in vacuo to give the product (3.33 g, 74%) having a boiling point of 65°–66° C. at 4 mm.

EXAMPLE 2A
Preparation of 2,6-bis-(5-trifluoromethylthienyl-3-oxy)-4-methylpyridine A mixture of 2,6-dichloro-4-methylpyridine (0.1 mol), 1D (potassium salt, 0.22 mol), and potassium carbonate (0.22 mol) in anhydrous sulfolane (70 ml) is heated to 80° C. for 4 hours and then to 100° C. for 3 hours. The reaction mixture is diluted with pentane/ethyl acetate (1/1 by volume). After filtration through a bed of silica gel the filtrate is washed 8 times with water. The organic layer is dried with anhydrous magnesium sulfate and filtered over silica gel. Now the solvent is removed and the residue is washed with diisopropyl ether. After drying, the product is obtained as an off-white wax of melting point 38°–39° C.

EXAMPLE 2B

By analogy to Example 2A, 2,6-bis-(5-trifluoromethylthienyl-3-oxy)-4-cyanopyridine can be obtained. This compound has a melting point of about 103°–104° C. It is identical to the compound of Example 2A, except for the cyano (in Example 2A, there is a methyl) substituent at the 4-position of the pyridine ring.

EXAMPLE 3
Preparation of 2-(3,4-difluorobenzyloxy)-6-(5-trifluoromethylthienyl-3-oxy)-4-methylpyridine To 0.34 g potassium tert-butylate (3 mmol) in 10 ml dry diglyme are added 0.51 g (3 mmol) 1D. After stirring at room temperature for 30 min., 0.55 g (2 mmol) 2-bromo-4-methyl-6-(3,4-difluorobenzyloxy)-pyridine (prepared analogously to the method disclosed in WO 94/22833), 0.3 g CuBr and a catalytic amount of 18-crown-6 ether are added. The mixture is heated to 130° C. under nitrogen atmosphere for 16 hrs. Another 0.51 g hydroxythiophene and 0.34 g potassium tert-butylate are added and heating is continued for 16 hrs. The mixture is diluted with toluene, washed with water and purified by flash chromatography. Yield 0.35 g oil

EXAMPLE 4
Preparation of 3,5-difluoro-2-(4-fluorobenzyloxy)-4-methyl-6-(5-trifluoromethylthienyl-3-oxy)-pyridine
4A 4-methyl-2,3,5-trifluoro-6-(5-trifluoromethylthienyl-3-oxy)-pyridine A mixture of 4-methyl-2,3,5,6-tetrafluoropyridine (20 mmol, 3.3 g), sodium hydride (23 mmol) and 1D (22 mmol, 3.7 g) in anhydrous acetonitrile (100 ml) is stirred at room temperature for 5 hours. The solvent is removed under reduced pressure. Pentane/ethyl acetate (1/1 by volume) is added to the residue and the mixture is washed twice with 2N sodium hydroxide and 5 times with water. After drying of the organic layer, the solvent is removed and the product is purified by flash chromatography and distillation under reduced pressure: One obtains the product of an oil (2.75 g, b.p. 110° C. at 0.0015 mbar).
4B 3,5-Difluoro-6-(4-fluorophenoxy)-4-methyl-2-(5-trifluoromethyl-thienyl-3-oxy)-pyridine A mixture of 4A (0.85 g, 2.7 mmol), 60% sodium hydride (0.13 g, 3.3 mmol) and 4-fluorobenzylalcohol (3,0 mmol) in anhydrous sulfolane (3 ml) is heated to 85° C. for 5 hours. The reaction mixture is diluted with pentane/ethyl acetate (1/1 by volume) and filtered through a bed of silica gel. The filtrate is washed 5 times with water, the organic layer is dried with anhydrous magnesium sulfate, and the solvents are removed in vacuo. The residue is purified by a flash silica gel chromatography using pentane/toluene in a ratio of 4/1. 0.6 g (53% yield) of 4B are obtained as a colourless oil.

EXAMPLES 5–34

Further Examples are prepared according to the general method of Example 3 or 4 and are listed in Table 1.

TABLE 1

| Ex. No. | $R^2$ | $R^3$ | $R^4$ | $Y^n$ | s | melting point (°C.) |
|---|---|---|---|---|---|---|
| 5 | $CH_3$ | 2-F | F | H | 1 | 55–57 |
| 6 | $CH_3$ | H | F | H | 1 | oil |
| 7 | $CH_3$ | 3-$CF_3$ | H | H | 0 | oil |
| 8 | CN | 3-Cl | Cl | H | 0 | oil |
| 9 | $CH_3$ | 3-F | F | F | 0 | oil |
| 10 | $CH_3$ | 3-Cl | F | F | 0 | oil |
| 11 | CN | H | H | H | 1 | oil |
| 12 | $CH_3$ | H | H | H | 1 | oil |
| 13 | $CH_3$ | 3-Cl | Cl | H | 0 | oil |
| 14 | $CH_3$ | 3-Cl | F | H | 0 | oil |
| 15 | $CH_3O$ | 2-F | F | H | 1 | |
| 16 | $CH_3O$ | H | F | H | 1 | |
| 17 | $CH_3O$ | 3-$CF_3$ | H | H | 0 | |
| 18 | $CH_3O$ | 3-F | F | F | 0 | |
| 19 | $CH_3O$ | H | F | F | 1 | |
| 20 | $CH_3O$ | 3-Cl | F | F | 0 | |
| 21 | $CH_3O$ | H | H | H | 1 | |
| 22 | $CH_3O$ | 3-Cl | Cl | H | 0 | |
| 23 | $CH_3O$ | 3-Cl | F | H | 0 | |
| 24 | H | 2-F | F | H | 1 | |
| 25 | H | H | F | H | 1 | |
| 26 | H | 3-$CF_3$ | H | H | 0 | |
| 27 | F | 3-F | F | F | 0 | |
| 28 | F | 3-F | F | F | 1 | |
| 29 | CN | H | F | H | 1 | oil |
| 30 | CN | 2-F | H | H | 1 | oil |
| 31 | $CH_3$ | H | H | F | 1 | oil |
| 32 | CN | 2-$CH_3$ | H | H | 1 | 78 |
| 33 | H | H | H | H | 1 | oil |
| 34 | CN | 3-$CF_3$ | H | H | 0 | oil |

EXAMPLE 35A
Preparation of 2-(thien-2-ylmethyloxy)-6-(5-trifluoromethylthienyl-3-oxy)-4-methylpyridine 2-bromo-4-methyl-6-(thien-2-ylmethoxy)-pyridine is reacted with 1D as described in example 3. After cooling, the reaction mixture is diluted with pentane/ethyl acetate (1/1 by volume) and filtered through a bed of silica gel. The filtrate is washed 6 times with water. The organic layer is dried with anhydrous magnesium sulfate, filtered and the solvents evaporate in vacuo. Purification by flash chromatography (2 times: silica gel, pentane/ethyl acetate 8/2 v/v and silica gel: toluene) gives the title compound as a colourless oil.

EXAMPLE 35B

By analogy to Example 35A, 4-cyano-2-(thien-2-ylmethoxy)-6-(5-trifluoromethylthienyl-3-oxy)-pyridine can be obtained. This compound has a melting point of about 54° C. It is identical to the compound of Example 35A, except for the cyano (in Example 35A, there is a methyl) substituent at the 4-position of the pyridine ring.

EXAMPLES 36–46

Further Examples are prepared according to the general method of Example 29 and are listed in Table 2.

TABLE 2

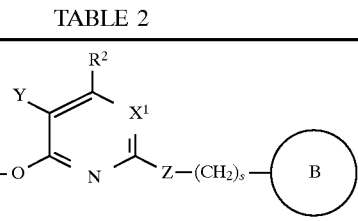

| Ex. No. | $R^2$ | B | Y | X' | Z | s |
|---|---|---|---|---|---|---|
| 36 | $CH_3$ | 1-$CH_3$-3-$CF_3$-pyrazol-5-yl | H | CH | O | 0 |
| 37 | $CH_3$ | 1-$CH_3$-3-$CF_3$-pyrazol-5-yl | F | CF | O | 0 |
| 38 | $CH_3O$ | 1-$CH_3$-3-$CF_3$-pyrazol-5-yl | H | CH | O | 0 |
| 39 | $CH_3O$ | 1-$CH_3$-3-$CF_3$-pyrazol-5-yl | F | CF | O | 0 |
| 40 | $CH_3$ | phenyl | H | CH | S | 1 |
| 41 | $CH_3$ | 3-$CF_3$-phenyl | H | CH | S | 0 |
| 42 | $CH_3O$ | 5-$CF_3$-thien-3-yl | H | N | O | 0 |
| 43 | $CH_3O$ | phenyl | H | N | O | 1 |
| 44 | $CH_3$ | 3-Cl-pyrid-4-yl | H | CH | O | 0 |
| 45 | $CH_3$ | 3-$CF_3$-pyrid-4-yl | H | CH | O | 0 |
| 46 | $CH_3$ | 3-$CF_2H$—O-pyrid-4-yl | H | CH | O | 0 |

Herbicidal Activity

To evaluate their herbicidal activity, compounds according to the invention are tested using a representative range of plants:

| | Plant Species Used | |
|---|---|---|
| TRZAW | Triticum aestivum | winter wheat |
| ZEAMX | Zea mays | maize |
| GLXMA | Glycine max | soybean |
| ALOMY | Alopecurus myosuroides | blackgrass |
| ECHCG | Echinichloa crus-galli | barnyardgrass |
| SETVI | Setaria viridis | green foxtail |
| ABUTH | Abutilon theophrasti | velvetlaef |
| GALAP | Galium aparine | cleaver |
| IPOHE | Ipomoea hederacea | morning glory |
| MATIN | Matricaria inodora | mayweed |
| CASOB | Senna obtusifolia | sicklepod |

The pre-emergence tests involve spraying a liquid formulation of the compound onto the soil in which the seeds of the plant species mentioned above has recently been sown. The soil used in the tests is a prepared horticultural loam. The formulations used in the tests are prepared from solutions of the test compounds in acetone containing 0.4% by weight of an alkylphenol/ethylene oxide condensate available under the trade mark TRITON X-155. These acetone solutions are diluted with water and the resulting formulations applied at dosage levels corresponding to 0.4 kg, of active material per hectare in a volume equivalent to 900 liters per hectare. In these tests untreated sown soil are used as controls.

The herbicidal effects of the test compounds are assessed visually twenty-one days after spraying the foliage and the soil and are recorded on a 0–9 scale. A rating 0 indicates growth as untreated control, a rating 9 indicates death. An increase of 1 unit on the linear scale approximates to a 10% increase in the level of effect. The results of the first assessment are set out in Table 3.

TABLE 3

Assessment (pre-emergence application) 21 days after treatment

| Example | GLXMA | TRZAW | ZEAMX | ALOMY | ECHCG | SETVI | ABUTH | CASOB | GALAP | IPOHE | MATIN |
|---|---|---|---|---|---|---|---|---|---|---|---|
| 2 | 4 | 6 | 6 | 9 | 9 | 9 | 9 | 9 | 7 | 9 | 9 |
| 3 | 5 | 5 | 5 | 9 | 9 | 9 | 9 | 9 |   | 9 | 8 |
| 4 | 5 | 5 | 4 | 9 | 9 | 9 | 8 | 9 | 8 | 8 | 9 |
| 5 | 5 | 3 | 5 | 9 | 9 | 9 | 8 | 9 | 8 | 9 | 9 |
| 6 | X | 4 | 6 | 9 | 9 | 9 | 9 | X | 8 | 9 | 9 |
| 7 | 1 | 4 | 3 | 9 | 8 | 9 | 7 | 7 |   | 6 | 8 |
| 8 | 2 | 3 | 3 | 7 | 9 | 9 | 3 | 5 |   | 1 | 9 |
| 9 | 4 | 5 | 5 | 9 | 9 | 9 | 9 | 7 |   | 9 | 8 |
| 10 | 3 | 4 | 4 | 9 | 9 | 9 | 5 | 9 |   | 3 | 9 |
| 11 | 4 | 1 | 5 | 9 | 9 | 9 | 9 | 9 |   | 9 | 9 |
| 12 | 4 | 2 | 5 | 9 | 9 | 9 | 9 | 8 |   | 8 | 9 |
| 13 | 4 | 3 | 2 | 8 | 8 | 9 | 8 | 9 |   | 8 | 9 |
| 14 | 3 | 3 | 3 | 9 | 8 | 9 | 9 | 9 |   | 5 | 9 |
| 29 | 2 | 1 | 4 | 9 | 8 | 9 | 6 | 9 |   | 1 | 8 |

X = no value
Assessment of cereals and maize: 10 days after treatment

The compounds of the invention have high activities against many weeds and show clearly improved selectivity in important crops (maize, soybeans, wheat, barley) when compared to the corresponding compounds of the state of the art having a 3-trifluoromethylphenoxy moiety instead of the 5-trifluoromethyl-thienyl-3-oxy - group according to the invention.

Post-emergence Herbicidal Evaluation of Test Compounds

The post-emergence herbicidal activity of the compounds of the present invention is demonstrated by the following test, wherein a variety of monocotyledonous and dicotyledonous plants are treated with formulations prepared from solutions of the test compounds in acetone containing 0,4% by weight of an alkylphenol/ethylene oxide condensate available under the trade mark TRITON X-155. These acetone solutions were diluted with water and the resulting formulations applied at dosage levels equivalent of about 0,4 kg per hectare of test compound per pot. After spraying the plants are placed on greenhouse benches and are cared for in the usual manner, commensurate with conventional greenhouse practices. From 2 to 4 weeks after treatment, the seedling plants are examined and rated according to the rating system provided below. A rating 0 indicates growth as untreated check, a rating 9 indicates death. The results of the tests are set out in Table 4 below. The compounds of the invention showed good performance on monocotyledonous and dicotyledonous weeds.

TABLE 4

| | Post-emergence application 21 days after treatment | | | | | | | | | |
|---|---|---|---|---|---|---|---|---|---|---|
| Example | GLXMA | TRZAW | ZEAMX | ALOMY | ECHCG | SETVI | ABUTH | CASOB | GALAP | IPOHE | MATIN |
| 2 | 8 | 4 | 6 | 8 | 8 | 8 | 6 | 8 | 7 | 9 | 6 |
| 3 | 7 | 5 | 6 | 8 | 8 | 9 | 7 | 7 | 8 | 9 | 7 |
| 4 | X | 5 | 5 | 8 | 8 | 8 | 5 | X | 7 | X | 5 |
| 5 | X | 5 | 5 | 8 | 9 | 8 | 7 | X | 7 | X | 6 |
| 6 | 8 | 4 | 5 | 8 | 8 | 9 | 6 | 7 | 7 | 9 | 6 |
| 9 | 7 | 5 | 6 | 8 | 8 | 9 | 6 | 5 | 8 | 9 | 6 |
| 12 | 7 | 4 | 6 | 8 | 8 | 9 | 6 | 7 | 8 | 9 | 7 |

X = no value
Assessment of cereals and maize: 10 days after treatment

What is claimed is:

1. A compound consisting essentially of formula (I)

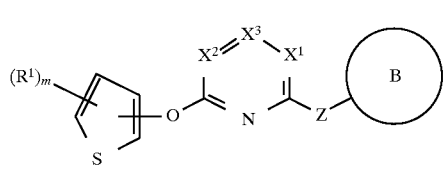

wherein the groups $X^1$, $X^2$ and $X^3$ represent CY, in which Y each independently represent a hydrogen atom or have the meaning given for $R^1$;

$R^1$ represents a halogen atom; an optionally substituted alkyl, alkenyl, alkinyl, alkoxy, alkoxyalkyl or alkoxyalkoxy group; a haloalkyl, haloalkoxy, cyano, nitro or $SF_5$ group; —$S(O)_p$—$R^3$, in which p is 0, 1 or 2, and $R^3$ represents an alkyl or haloalkyl group; $NR^4R^5$, in which $R^4$ and $R^5$ each independently represent a hydrogen atom, an alkyl, alkenyl, aralkyl or aryl group; or $R^6O$—$CY'$—, in which $R^6$ represents an alkyl group, and Y' represents O or S;

B represents a radical selected from the group consisting of

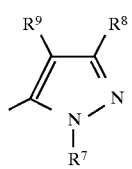

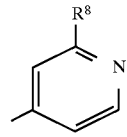

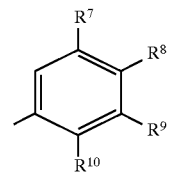

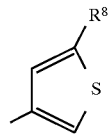

wherein $R^7$ to $R^{10}$ each independently represent a hydrogen or halogen atom, or an optionally substituted alkyl or alkoxy group;

Z represents an oxygen or sulfur atom or a —$OCH_2$— or —$SCH_2$— group; and m is 0 or an integer from 1 to 3.

2. A compound as claimed in claim 1, wherein Z represents an oxygen atom or a —$OCH_2$— group.

3. A compound as claimed in claim 1, wherein $R^1$ represents a halogen atom or a haloalkyl group.

4. A compound as claimed in claim 3, having the formula

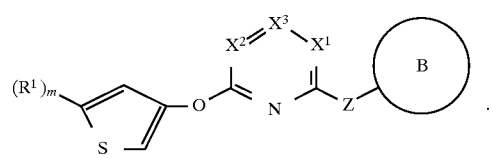

5. A compound as claimed in claim 1, wherein $X^3$ represents $CR^2$.

6. A compound consisting essentially of formula IA $$\text{(IA)}$$

wherein either

R$^1$ and R$^2$ each independently represent a halogen atom; an optionally substituted alkyl, alkenyl, alkinyl, alkoxy, alkoxyalkyl or alkoxyalkoxy group; a haloalkyl, haloalkoxy, cyano, nitro or SF$_5$ group; -S(O)$_p$-R$^3$, in which p is 0, 1 or 2, and R$^3$ represents an alkyl or haloalkyl group;

—NR$^4$R$^5$, in which R$^4$ and R$^5$ each independently represent a hydrogen atom, an alkyl, alkenyl, aralkyl or aryl group; or R$^6$O—CY'—, in which R$^6$ represents an alkyl group, and Y' represents O or S; or R$^1$ is as described above and R$^2$ is hydrogen;

R$^3$ and R$^4$ each independently represent a hydrogen or halogen atom, or a haloalkyl group;

Y" represents a hydrogen or fluorine atom; and s is 0 or 1.

7. The compound as claimed in claim 6, wherein R$^2$ is hydrogen, a C$_1$ to C$_4$ alkyl or alkoxy group, or cyano.

8. The compound as claimed in claim 7, wherein R$^2$ is hydrogen, C$_1$ to C$_4$ alkyl or cyano.

9. The compound as claimed in claim 6 wherein R$^2$ is methyl.

10. The compound as claimed in claim 6, wherein R$^1$ is trifluoromethyl.

11. A compound according to claim 1 selected from the group consisting of 2,6-bis-(5-trifluoromethylthien-3-yloxy)-4-methylpyridine, 2-(4-fluorobenzyloxy)-6-(5-trifluoromethylthien-3-yloxy)-4-methylpyridine, 2-(3,4-difluorobenzyloxy)-6-(5-trifluoromethylthien-3-yloxy)-4-methylpyridine, 2-(2,4-difluorobenzyloxy)-6-(5-trifluoromethylthien-3-yloxy)-4-methylpyridine, 2-(3-trifluoromethylphenoxy)-6-(5-trifluoromethylthien-3-yloxy)-4-methylpyridine, 2-(3,4-dichlorophenoxy)-6-(5-trifluoromethylthien-3-yloxy)-4-cyanopyridine, 2-(3,4-dichlorophenoxy)-6-(5-trifluoromethylthien-3-yloxy)-4-methylpyridine, 3,5-difluoro-2-(4-fluorobenzyloxy)-6-(5-trifluoromethylthien-3-yloxy)-4-methylpyridine, 3,5-difluoro-2-(3,4-difluorophenoxy)-6-(5-trifluoromethylthien-3-yloxy)-4-methylpyridine, 3,5-difluoro-2-(3-chloro-4-fluorophenoxy)-6-(5-trifluoromethylthien-3-yloxy)-4-methylpyridine, 2-benzyloxy-6-(5-trifluoromethylthien-3-yloxy)-4-cyanopyridine, 2-benzyloxy-6-(5-trifluoromethylthien-3-yloxy)-4-methylpyridine, 2-(3-chloro-4-fluorophenoxy)-6-(5-trifluoromethylthien-3-yloxy)-4-methylpyridine, 2-(thien-2-ylmethyloxy)-6-(5-trifluoromethylthien-3-yloxy)-4-methylpyridine, 2-(2,4-difluorobenzyloxy)-6-(5-trifluoromethylthien-3-yloxy)-4-methoxypyridine, 2-(4-fluorobenzyloxy)-6-(5-trifluoromethylthien-3-yloxy)-4-methoxypyridine, 2-(3-trifluoromethylphenyloxy)-6-(5-trifluoromethylthien-3-yloxy)-4-methoxypyridine, 3,5-difluoro-2-(3-fluorophenoxy)-6-(5-trifluoromethylthien-3-yloxy)-4-methoxypyridine, 3,5-difluoro-2-benzyloxy-6-(5-trifluoromethylthien-3-yloxy)-4-methoxypyridine, 3,5-difluoro-2-(3-chlorophenoxy)-6-(5-trifluoromethylthien-3-yloxy)-4-methoxypyridine, 2-benzyloxy-6-(5-trifluoromethylthien-3-yloxy)-4-methoxypyridine, 2-(3,4-dichlorophenoxy)-6-(5-trifluoromethylthien-3-yloxy)-4-methoxypyridine, 2-(3-chloro-4-fluorophenoxy)-6-(5-trifluoromethylthien-3-yloxy)-4-methoxypyridine, 2-(2,4-difluorobenzyloxy)-6-(5-trifluoromethylthien-3-yloxy)-pyridine, 2-(4-fluorobenzyloxy)-6-(5-trifluoromethylthien-3-yloxy)-pyridine, 2-(3-trifluoromethylphenyloxy)-6-(5-trifluoromethylthien-3-yloxy)-pyridine, 3,4,5-trifluoro-2-(3,4-difluorophenoxy)-6-(5-trifluoromethylthien-3-yloxy)-pyridine, 3,4,5-trifluoro-2-(3,4-difluorobenzyloxy)-6-(5-trifluoromethylthien-3-yloxy)-pyridine, 2-benzylthio-6-(5-trifluoromethylthienyl-3-oxy)-4-methylpyridine, 2-(3-triflurmethylphenylthio)-6-(5-trifluoromethylthienyl-3-oxy)-4-methylpyridine, 2-(3-chloropryid-4-yloxy)-6-(5-trifluoromethylthienyl-3-oxy)-4-methylpyridine, 2-(3-trifluoromethylpyrid-4-yloxy)-6-(5-trifluoromethylthienyl-3-oxy)-4-methylpyridine, 2-(3-difluoromethoxypyrid-4-yloxy)-6-(5-trifluoromethylthienyl-3-oxy)-4-methylpyridine, and 2-(1-methyl-3-trifluoromethylpyrazol-5-yloxy)-6-(5-trifluoromethylthienyl-3-oxy)-4-methylpyridine.

12. A process for the preparation of the compound of claim 1 which comprises reacting a compound of formula II $$\text{(II)}$$

in which R$^1$, R$^2$, X$^1$ to X$^3$ and m are as described for formula I, with a compound of formula III or a metal salt thereof $$\text{(III)}$$

in which B an Z are as described above.

13. Process for the preparation of a compound of formula II in claim 12

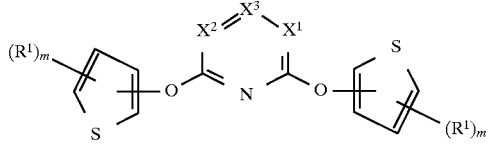 (II)

which comprises reacting a compound of formula IV

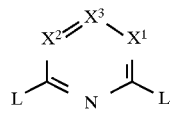 (IV)

in which $X^1$ to $X^3$ are as described for formula II, and L is a leaving group, with compound of formula V or a metal salt thereof

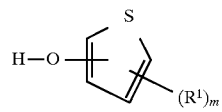 (V)

in which $R^1$ and m are as described above.

14. A herbicidal composition comprising at least one compound as claimed in claim 1, and a carrier.

15. Composition as claimed in claim 14, comprising at least two carriers, a least one of the carriers being is a surface-active agent.

16. A method of combating undesired plant growth at a locus, comprising applying to the locus the compound as claimed in claim 1 or the composition as claimed in claim 14.

17. A method for the control of monocotyledenous and dicotyledonous annual, perennial and aquatic plant species which comprises applying to the foliage of said plants, or to the soil or water containing the seeds or other propagating organs thereof a herbicidally effective amount of the compound of claim 1 or the composition of claim 14.

* * * * *